(12) United States Patent
Siochi

(10) Patent No.: US 6,314,159 B1
(45) Date of Patent: Nov. 6, 2001

(54) SYSTEM AND METHOD FOR OPTIMIZING RADIATION TREATMENT WITH AN INTENSITY MODULATING MULTI-LEAF COLLIMATOR

(75) Inventor: Ramon Alfredo Carvalho Siochi, Apex, NC (US)

(73) Assignee: Siemens Medical Systems, Inc., Iselin, NJ (US)

( * ) Notice: Subject to any disclaimer, the term of this patent is extended or adjusted under 35 U.S.C. 154(b) by 0 days.

(21) Appl. No.: 09/457,602

(22) Filed: Dec. 8, 1999

(51) Int. Cl.⁷ ....................................................... A61N 5/10
(52) U.S. Cl. ............................ 378/65; 378/64; 250/492.3
(58) Field of Search ............................ 378/5, 64, 65, 378/147, 160

(56) References Cited

U.S. PATENT DOCUMENTS

| | | | |
|---|---|---|---|
| 5,663,999 | 9/1997 | Siochi | 378/65 |
| 5,724,403 | 3/1998 | Siochi et al. | 378/150 |
| 6,134,296 | * 10/2000 | Siochi | 378/65 |

* cited by examiner

*Primary Examiner*—Robert H. Kim
*Assistant Examiner*—Courtney Thomas

(57) ABSTRACT

A method for controlling radiation delivery from a radiation source to an object is disclosed. The method includes defining a field on the object for radiation delivery. The field includes a plurality of cells, each cell having a defined treatment intensity level. The cells are grouped to form a matrix having at least one dimension approximately equal to a width of a collimator leaf capable of blocking radiation emitted from the radiation source. The method further includes decomposing the matrix into orthogonal matrices and optimizing delivery of the radiation by selecting the orthogonal matrices having minimum vertical and horizontal gradients when combined with adjacent cells. A system for controlling radiation delivery from a radiation source to an object is also disclosed.

20 Claims, 10 Drawing Sheets

$$V = \begin{array}{|c|c|c|c|} \hline 1 & 2 & 3 & 4 \\ \hline 3 & 4 & 5 & 6 \\ \hline \end{array}$$

$$v1,1 = \begin{array}{|c|c|} \hline 1 & 2 \\ \hline 3 & 4 \\ \hline \end{array} \qquad v1,3 = \begin{array}{|c|c|} \hline 3 & 4 \\ \hline 5 & 6 \\ \hline \end{array}$$

FIG. 9

$$u1,1 = \begin{array}{|c|c|} \hline 1 & 1 \\ \hline 1 & 1 \\ \hline \end{array} \qquad u1,3 = \begin{array}{|c|c|} \hline 3 & 3 \\ \hline 3 & 3 \\ \hline \end{array}$$

FIG. 10

$$m1,1 = \begin{array}{|c|c|} \hline 0 & 1 \\ \hline 2 & 3 \\ \hline \end{array} \qquad m1,3 = \begin{array}{|c|c|} \hline 0 & 1 \\ \hline 2 & 3 \\ \hline \end{array}$$

FIG. 11

$90_{m1,1}=\begin{array}{|c|c|}\hline 0 & 0 \\\hline 2 & 2 \\\hline\end{array}$  $90_{m1,3}=\begin{array}{|c|c|}\hline 0 & 0 \\\hline 2 & 2 \\\hline\end{array}$  $0_{m1,1}=\begin{array}{|c|c|}\hline 0 & 1 \\\hline 0 & 1 \\\hline\end{array}$  $0_{m1,3}=\begin{array}{|c|c|}\hline 0 & 1 \\\hline 0 & 1 \\\hline\end{array}$

FIG. 12

$90_{u1,1}=\begin{array}{|c|c|}\hline 0 & 0 \\\hline 0 & 0 \\\hline\end{array}$  $90_{u1,3}=\begin{array}{|c|c|}\hline 0 & 0 \\\hline 0 & 0 \\\hline\end{array}$  $0_{u1,1}=\begin{array}{|c|c|}\hline 1 & 1 \\\hline 1 & 1 \\\hline\end{array}$  $0_{u1,3}=\begin{array}{|c|c|}\hline 3 & 3 \\\hline 3 & 3 \\\hline\end{array}$

FIG. 13a $90_{u1,1}=\begin{array}{|c|c|}\hline 0 & 0 \\\hline 0 & 0 \\\hline\end{array}$  $90_{u1,3}=\begin{array}{|c|c|}\hline 1 & 1 \\\hline 1 & 1 \\\hline\end{array}$  $0_{u1,1}=\begin{array}{|c|c|}\hline 1 & 1 \\\hline 1 & 1 \\\hline\end{array}$  $0_{u1,3}=\begin{array}{|c|c|}\hline 2 & 2 \\\hline 2 & 2 \\\hline\end{array}$

FIG. 13b $90_{u1,1}=\begin{array}{|c|c|}\hline 0 & 0 \\\hline 0 & 0 \\\hline\end{array}$  $90_{u1,3}=\begin{array}{|c|c|}\hline 2 & 2 \\\hline 2 & 2 \\\hline\end{array}$  $0_{u1,1}=\begin{array}{|c|c|}\hline 1 & 1 \\\hline 1 & 1 \\\hline\end{array}$  $0_{u1,3}=\begin{array}{|c|c|}\hline 1 & 1 \\\hline 1 & 1 \\\hline\end{array}$

FIG. 13c $90_{u1,1} = \begin{array}{|c|c|} \hline 0 & 0 \\ \hline 0 & 0 \\ \hline \end{array}$  $90_{u1,3} = \begin{array}{|c|c|} \hline 3 & 3 \\ \hline 3 & 3 \\ \hline \end{array}$  $0_{u1,1} = \begin{array}{|c|c|} \hline 1 & 1 \\ \hline 1 & 1 \\ \hline \end{array}$  $0_{u1,3} = \begin{array}{|c|c|} \hline 0 & 0 \\ \hline 0 & 0 \\ \hline \end{array}$

FIG. 13d $90_{u1,1} = \begin{array}{|c|c|} \hline 1 & 1 \\ \hline 1 & 1 \\ \hline \end{array}$  $90_{u1,3} = \begin{array}{|c|c|} \hline 0 & 0 \\ \hline 0 & 0 \\ \hline \end{array}$  $0_{u1,1} = \begin{array}{|c|c|} \hline 0 & 0 \\ \hline 0 & 0 \\ \hline \end{array}$  $0_{u1,3} = \begin{array}{|c|c|} \hline 3 & 3 \\ \hline 3 & 3 \\ \hline \end{array}$

FIG. 13e $90_{u1,1} = \begin{array}{|c|c|} \hline 1 & 1 \\ \hline 1 & 1 \\ \hline \end{array}$  $90_{u1,3} = \begin{array}{|c|c|} \hline 1 & 1 \\ \hline 1 & 1 \\ \hline \end{array}$  $0_{u1,1} = \begin{array}{|c|c|} \hline 0 & 0 \\ \hline 0 & 0 \\ \hline \end{array}$  $0_{u1,3} = \begin{array}{|c|c|} \hline 2 & 2 \\ \hline 2 & 2 \\ \hline \end{array}$

FIG. 13f $90_{u1,1} = \begin{array}{|c|c|} \hline 1 & 1 \\ \hline 1 & 1 \\ \hline \end{array}$  $90_{u1,3} = \begin{array}{|c|c|} \hline 2 & 2 \\ \hline 2 & 2 \\ \hline \end{array}$  $0_{u1,1} = \begin{array}{|c|c|} \hline 0 & 0 \\ \hline 0 & 0 \\ \hline \end{array}$  $0_{u1,3} = \begin{array}{|c|c|} \hline 1 & 1 \\ \hline 1 & 1 \\ \hline \end{array}$

FIG. 13g $90_{u1,1} = \begin{array}{|c|c|} \hline 1 & 1 \\ \hline 1 & 1 \\ \hline \end{array}$  $90_{u1,3} = \begin{array}{|c|c|} \hline 3 & 3 \\ \hline 3 & 3 \\ \hline \end{array}$  $0_{u1,1} = \begin{array}{|c|c|} \hline 0 & 0 \\ \hline 0 & 0 \\ \hline \end{array}$  $0_{u1,3} = \begin{array}{|c|c|} \hline 0 & 0 \\ \hline 0 & 0 \\ \hline \end{array}$

SYSTEM AND METHOD FOR OPTIMIZING RADIATION TREATMENT WITH AN INTENSITY MODULATING MULTI-LEAF COLLIMATOR

FIELD OF THE INVENTION

The present invention relates generally to a radiation emitting device, and more particularly, to a system and method for efficiently delivering radiation treatment.

BACKGROUND OF THE INVENTION

Radiation emitting devices are generally known and used, for instance, as radiation therapy devices for the treatment of patients. A radiation therapy device generally includes a gantry which can be swiveled around a horizontal axis of rotation in the course of a therapeutic treatment. A linear accelerator is located within the gantry for generating a high energy radiation beam for therapy. This high energy radiation beam may be an electron beam or photon (x-ray) beam, for example. During treatment, the radiation beam is trained on a zone of a patient lying in the isocenter of the gantry rotation.

In order to control the radiation emitted toward the patient, a beam shielding device, such as a plate arrangement or collimator, is typically provided in the trajectory of the radiation beam between the radiation source and the patient. An example of a plate arrangement is a set of four plates which can be used to define an opening for the radiation beam. The collimator is a beam shielding device which may include multiple leaves (e.g., relatively thin plates or rods) typically arranged as opposing leaf pairs. The plates are formed of a relatively dense and radiation impervious material and are generally independently positionable to delimit the radiation beam.

The beam shielding device defines a field on the zone of the patient for which a prescribed amount of radiation is to be delivered. The usual treatment field shape results in a three-dimensional treatment volume which includes segments of normal tissue, thereby limiting the dose that can be given to the tumor. The dose delivered to the tumor can be increased if the amount of normal tissue being irradiated is decreased and the dose delivered to the normal tissue is decreased. Avoidance of delivery of radiation to the healthy organs surrounding and overlying the tumor limits the dosage that can be delivered to the tumor.

The delivery of radiation by a radiation therapy device is typically prescribed by an oncologist. The prescription is a definition of a particular volume and level of radiation permitted to be delivered to that volume. Actual operation of the radiation equipment, however, is normally done by a therapist. The radiation emitting device is programmed to deliver the specific treatment prescribed by the oncologist. When programming the device for treatment, the therapist has to take into account the actual radiation output and has to adjust the dose delivery based on the plate arrangement opening to achieve the prescribed radiation treatment at the desired depth in the target.

The radiation therapist's challenge is to determine the best number of fields and intensity levels to optimize dose volume histograms, which define a cumulative level of radiation that is to be delivered to a specified volume. Typical optimization engines optimize the dose volume histograms by considering the oncologist's prescription, or three-dimensional specification of the dosage to be delivered. In such optimization engines, the three-dimensional volume is broken into cells, each cell defining a particular level of radiation to be administered. The outputs of the optimization engines are intensity maps, which are determined by varying the intensity at each cell in the map. The intensity maps specify a number of fields defining optimized intensity levels at each cell. The fields may be statically or dynamically modulated, such that a different accumulated dosage is received at different points in the field. Once radiation has been delivered according to the intensity map, the accumulated dosage at each cell, or dose volume histogram, should correspond to the prescription as closely as possible.

In such intensity modulation, borders between critical structures and tumor volumes are sometimes not well approximated with a standard one centimeter width leaf which provides a one centimeter by one centimeter grid (cell size) over the intensity map. A higher resolution than typically provided with the one centimeter leaf is often required. One possible solution is to provide a collimator with thinner leaves. However, the additional hardware required for the additional leaves is expensive, adds weight to the system, may reduce clearance between the treatment head and the patient, and may decrease reliability and life of the system.

Accordingly, there is therefore, a need for a system and method for achieving higher spatial resolution intensity modulation radiation therapy without changing current multi-leaf collimator leaf widths and an optimization for such a system and method to minimize treatment time.

SUMMARY OF THE INVENTION

A method and system for controlling radiation delivery from a radiation source to an object are disclosed.

A method of the present invention generally comprises defining a field on the object for radiation delivery. The field includes a plurality of cells, each having a defined treatment intensity level. The cells are grouped to form a matrix having at least one dimension approximately equal to a width of a collimator leaf capable of blocking radiation emitted from the radiation source. The method further includes decomposing the matrix into orthogonal matrices and optimizing delivery of the radiation by selecting the orthogonal matrices having minimum vertical and horizontal gradients when combined with adjacent cells within the field.

A system of the present invention generally comprises a collimator having multiple leaves for blocking radiation from the source and defining an opening between the radiation source and object. The system further includes a processor for receiving a matrix comprising a plurality of cells having at least one dimension approximately equal to a width of one of the collimator leaves, decomposing the matrix into orthogonal matrices, and optimizing delivery of the radiation output by selecting the orthogonal matrices having minimum vertical and horizontal gradients when combined with adjacent cells within the field.

The above is a brief description of some deficiencies in the prior art and advantages of the present invention. Other features, advantages, and embodiments of the invention will be apparent to those skilled in the art from the following description, drawings, and claims.

BRIEF DESCRIPTION OF THE DRAWINGS

FIG. 8 is a diagram of a macromatrix used to illustrate an example of an optimization process of the present invention.

FIG. 9 is a diagram of two micromatrices of the macromatrix of FIG. 8.

FIG. 10 is a diagram of uniform matrices formed from the micromatrices of FIG. 9 for use in the optimization process.

FIG. 11 is a diagram of microgradient matrices formed from the micromatrices of FIG. 9 for use in the optimization process.

FIG. 12 illustrates the microgradient matrices of FIG. 11 broken into zero degree offset and ninety degree offset matrices.

FIGS. 13a–13h illustrate different possible zero degree offset and ninety degree offset uniform matrices based on the uniform matrices of FIG. 10.

FIGS. 14a–14h illustrate different possible total matrices defined in the optimization process and used to determine an optimum treatment delivery process.

Corresponding reference characters indicate corresponding parts throughout the several views of the drawings.

DETAILED DESCRIPTION OF THE PREFERRED EMBODIMENTS

The following description is presented to enable one of ordinary skill in the art to make and use the invention and is provided in the context of a patent application and its requirements. Various modifications to the preferred embodiments will be readily apparent to those skilled in the art and the generic principles herein may be applied to other embodiments. Thus, the present invention is not intended to be limited to the embodiment shown but is to be accorded the widest scope consistent with the principles and features described herein.

Figure 1:
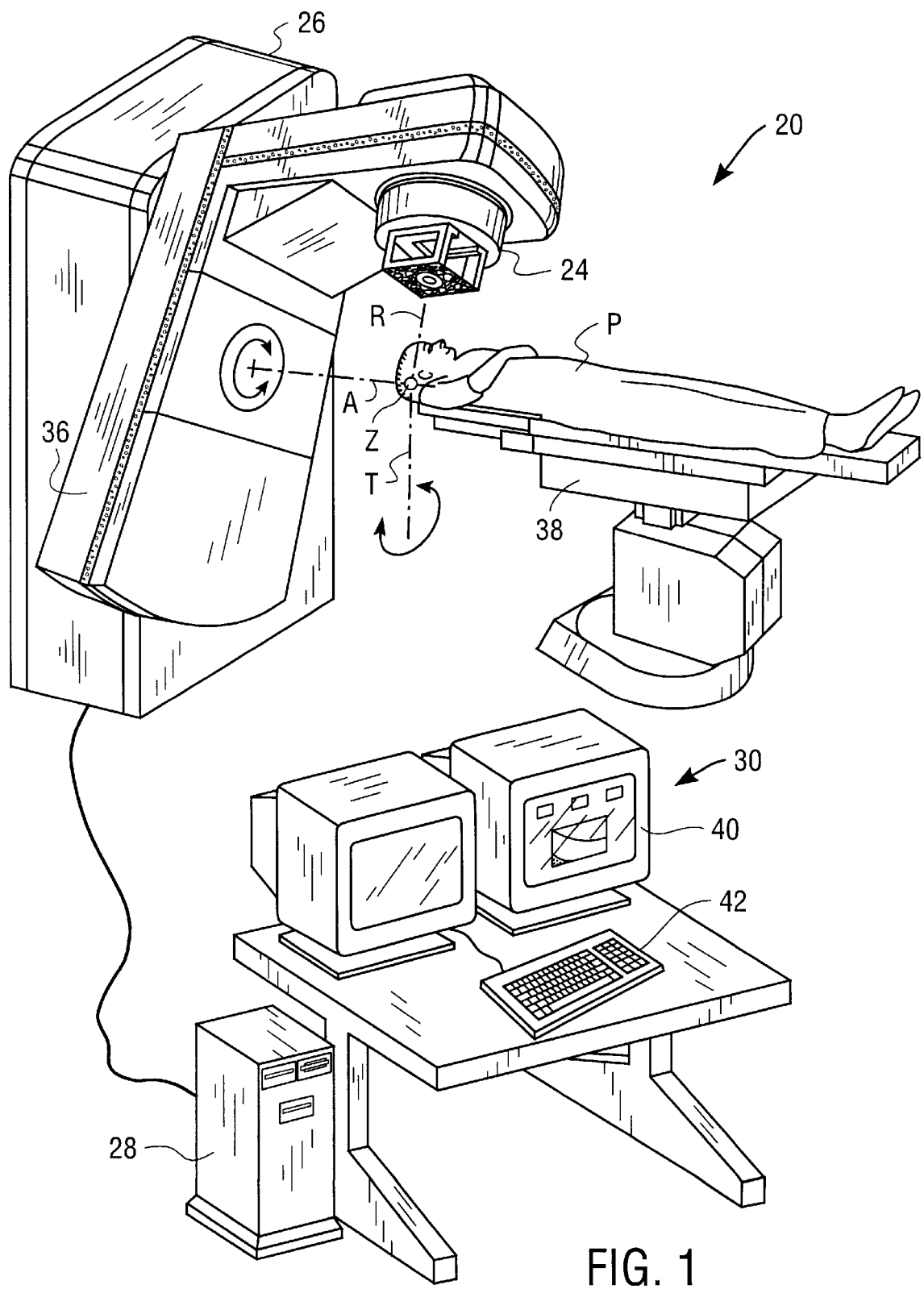
FIG. 1 is a diagram of a radiation treatment device and treatment console according to an embodiment of the present invention and a patient positioned for treatment within the treatment device.

Referring now to the drawings, and first to FIG. 1, a radiation treatment device of the present invention is shown and generally indicated at 20. The radiation treatment device 20 includes a beam shielding device (not shown) within a treatment head 24, a control unit within a housing 26 connected to a treatment processing unit, generally indicated at 30. The radiation treatment device further includes a gantry 36 which can be swiveled for rotation about axis A in the course of a therapeutic treatment. The treatment head 24 is fixed to the gantry 36 for movement therewith and a linear accelerator is located within the gantry for generating high powered radiation used for therapy. The radiation emitted from the linear accelerator extends generally along axis R. Electron, photon, or any other detectable radiation may be used for the therapy. During treatment, the radiation beam is focused on a zone Z of an object P (e.g., a patient who is to be treated). The zone to be treated is located at an isocenter defined by the intersection of the rotational axis A of the gantry 36, rotational axis T of treatment table 38, and the radiation beam axis R. The rotatable gantry 36 allows for different beam angles and radiation distributions without having to move the patient.

The treatment processing unit 30 is used to input information, such as radiation intensity and location of treatment, into the radiation treatment device 20 and output data for monitoring of the treatment. The processing unit 30 includes an output device such as a visual display monitor 40 and an input device such as a keyboard 42. The treatment processing unit 30 is typically operated by a therapist who administers actual delivery of radiation treatment as prescribed by an oncologist. The therapist uses the keyboard 42 to enter data, which defines the radiation dose to be delivered to the patient, into the processing unit 30. The data may also be input via other input devices, such as a data storage device, for example. Various types of data can be displayed before and during the treatment on the screen of the display monitor 40.

Figure 2:
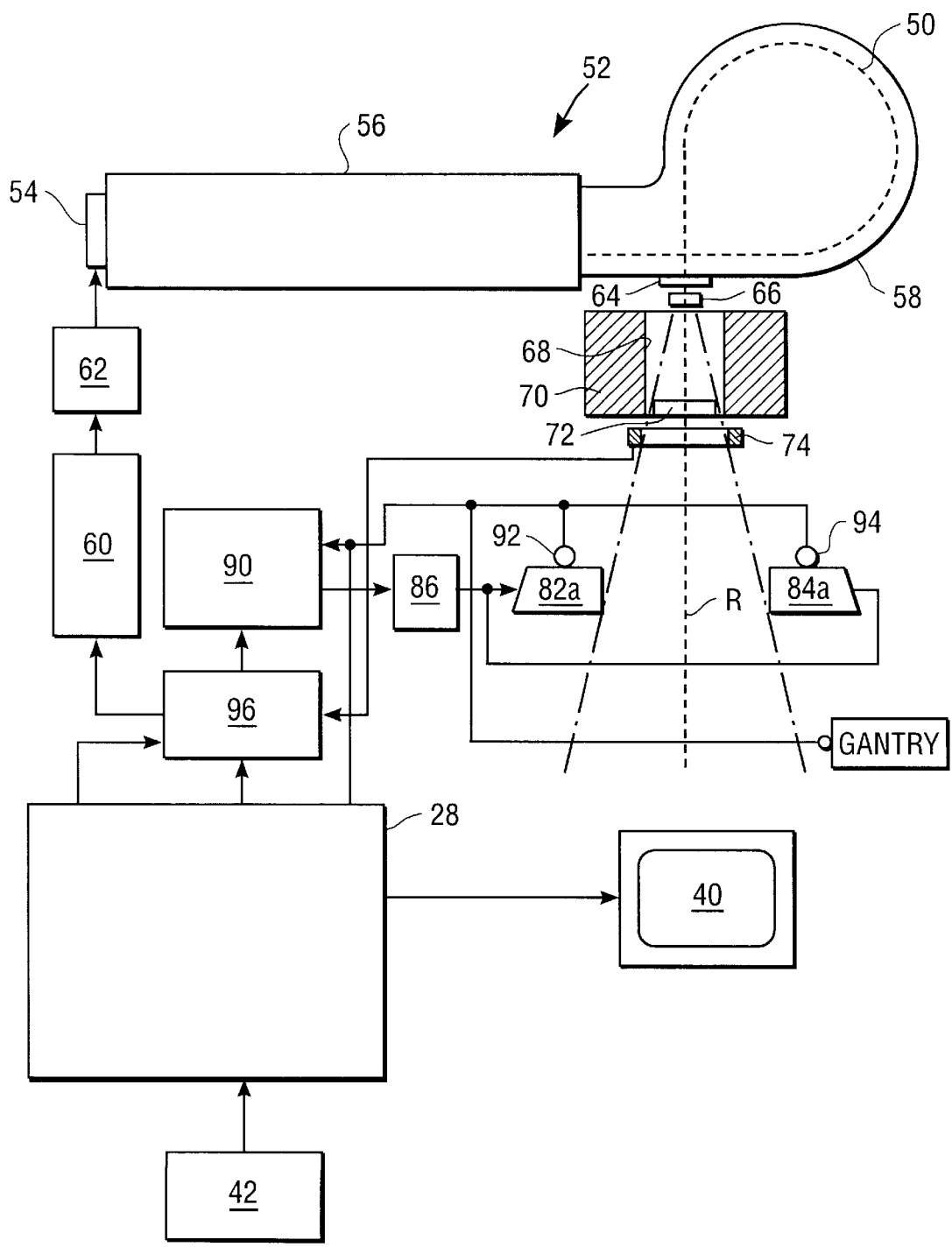
FIG. 2 is a block diagram illustrating portions of the radiation treatment device of FIG. 1.

FIG. 2 is a block diagram of the radiation treatment device 20 showing portions of the treatment processing unit 30 in further detail. An electron beam 50 is generated in an electron accelerator, generally indicated at 52. The electron accelerator 52 includes an electron gun 54, wave guide 56, and an evacuated envelope or guide magnet 58. A trigger system 60 generates injector trigger signals and supplies them to an injector 62. Based on these injector trigger signals, the injector 62 generates injector pulses which are fed to the electron gun 54 in the accelerator 52 for generating electron beam 50. The electron beam 50 is accelerated and guided by the wave guide 56. For this purpose, a high frequency source (not shown) is provided, which supplies radio frequency signals for the generation of an electromagnetic field supplied to the wave guide 56. The electrons injected by the injector 62 and emitted by the electron gun 54 are accelerated by the electromagnetic field in the wave guide 56 and exit at the end opposite the electron gun 54 to form electron beam 50. The electron beam 50 then enters the guide magnet 58 and from there is guided through a window 64 along axis R. After passing through a scattering foil 66 for electron mode (or target for photon mode), the beam 50 passes through a passageway 68 of a shield block 70 and encounters a secondary scattering foil 72 for electron mode (or flattening filter for photon mode). The beam next passes through a measuring chamber 74 in which the dose is ascertained.

Figure 3:
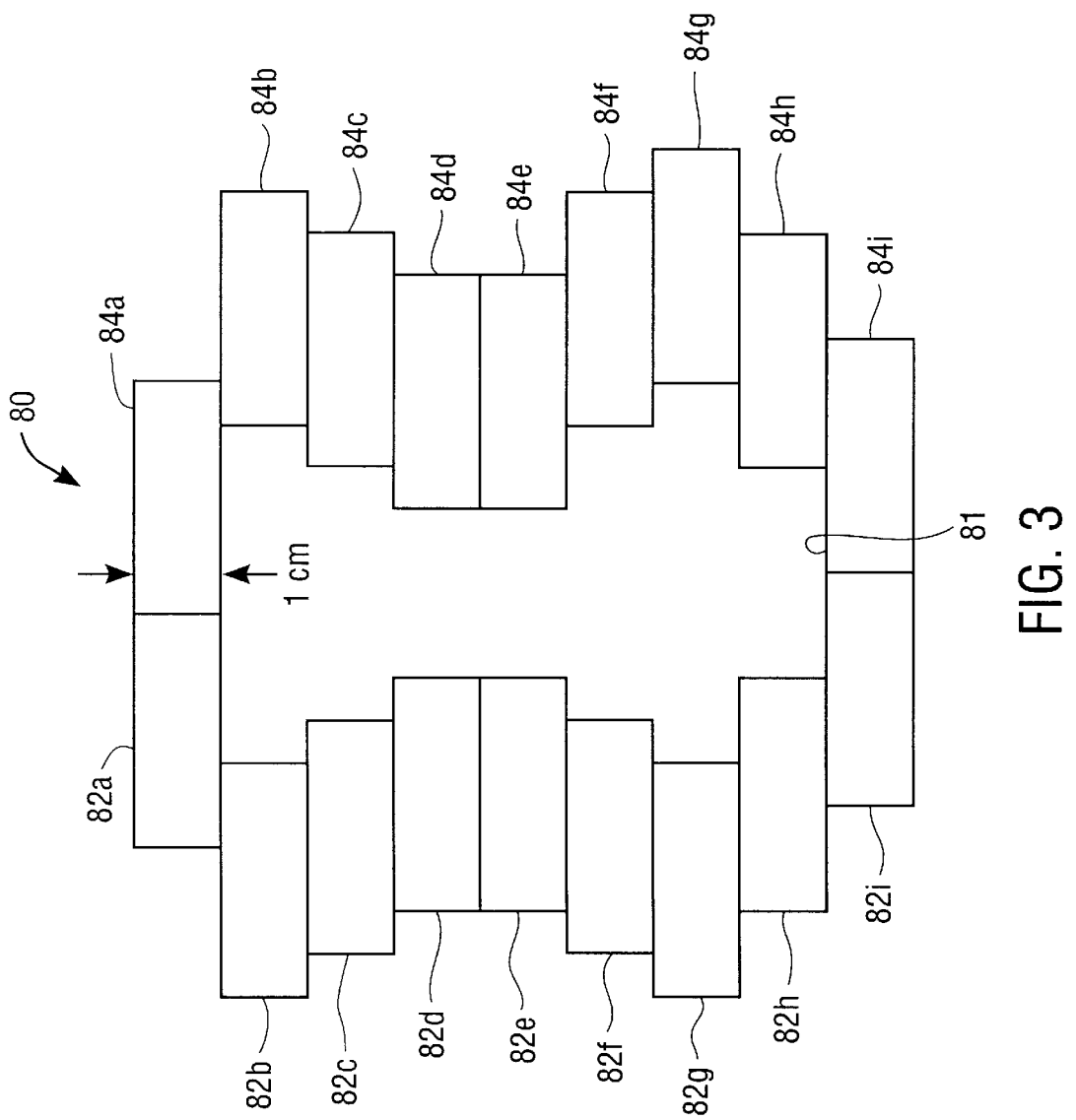
FIG. 3 is a schematic illustrating leaves of a multi-leaf collimator positioned for treatment in the radiation treatment device of FIG. 1.

A beam shielding device, generally indicated at 80, is provided in the path of the beam 50 to define a radiation field 81 (FIGS. 2 and 3). The beam shielding device 80 includes a plurality of opposing plates or leaves 82a–i and 84a–i, only two of which are shown in FIG. 2 for simplification. FIG. 3 illustrates leaves 82a–i and 84a–i (forming leaf pairs 82a and 84a, 82b and 84b, . . . , 82i and 84i ) of a multi-leaf collimator mounted between the radiation source and patient and positioned to define a treatment field by delimiting the electron beam 50. The leaves 82a–i, 84a–i typically have a one centimeter width and are substantially impervious to the emitted radiation so that they block healthy tissue from the radiation. The leaves 82a–i, 84a–i are movable in a direction generally perpendicular to axis R by a drive unit 86 (which is shown in FIG. 2 only with respect to plate 82a) to change the size of the irradiated field so that the distribution of radiation over the field does not need to be uniform (i.e., one region may be exposed to a higher dose than another region). The drive unit 86 includes an electric motor which is coupled to the plate 82a and controlled by a motor controller 90. Position sensors 92, 94 are also coupled to plates 82a, 84a, respectively, for sensing their positions. The drive unit 86 drives the plate 82a in and out of the treatment field, thus creating the desired field shapes.

The motor controller 90 is coupled to a dose control unit 96 which includes a dosimetry controller coupled to the central processing unit 28 for providing set values for the radiation beam for achieving given isodose curves (FIG. 2). The output of the radiation beam is measured by the measuring chamber 74. In response to the deviation between the set values and the actual values, the dose control unit 96 supplies signals to the trigger system 60 which change in a known manner the pulse repetition frequency so that the deviation between the set values and the actual values of the radiation beam output is minimized. The dose absorbed by the patient is dependent upon movement of the collimator plates 82a, 84a. The central processing unit 28 controls execution of the program and the opening and closing of the collimator plates 82a, 84a to deliver radiation according to a desired intensity profile. The central processing unit 28 may include other features described in U.S. Pat. No. 5,724,403, which is incorporated herein by reference in its entirety, for example.

It is to be understood that the radiation treatment device may be different than the one described and shown herein without departing from the scope of the invention.

The treatment device 20 described above is provided as an example of a device for use in delivering a treatment developed by the optimization process described below.

Figure 4:
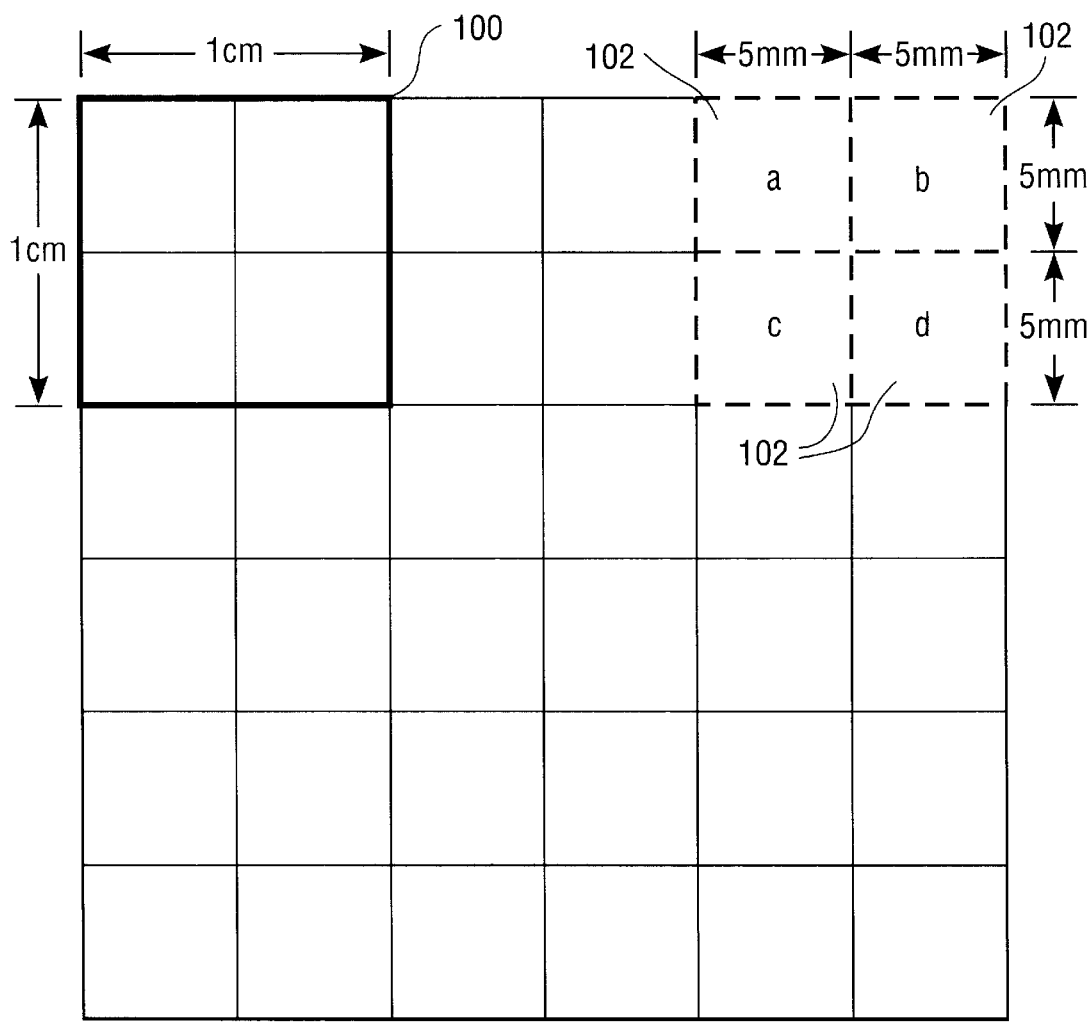
FIG. 4 is a schematic illustrating cells located in an intensity map.

FIG. 4 illustrates an intensity map having a plurality of 1 cm×1 cm macrocells 100 (indicated by dark lines) divided into four 5 mm×5 mm microcells 102 (indicated by dashed lines). The 5 mm×5 mm microcells 102 are used to convert macrocell 100 into two orthogonal intensity maps, one with a resolution of 5 mm×10 mm, and the other with a resolution of 10 mm×5 mm. An example of a process for dividing the intensity map into groups of four 5 mm×5 mm microcells 102 is described in U.S. patent application Ser. No. 09/234,364, by Siochi, filed Jan. 20, 1999, which is incorporated herein by reference in its entirety. This grouping of 5 mm×5 mm microcells 102 allows for treatment of a field with a 5 mm×5 mm resolution using a multi-leaf collimator having one centimeter leaves, as shown in FIG. 3.

Figure 5:
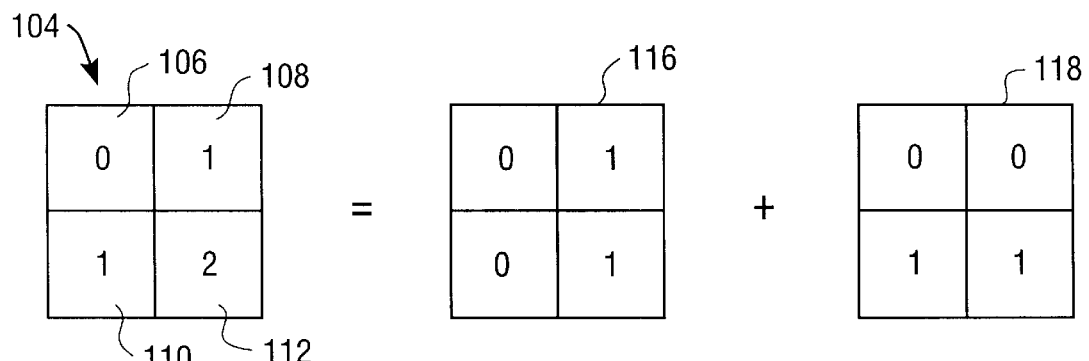
FIG. 5 is a diagram of a matrix broken down into a zero degree matrix component and a ninety degree matrix component.
Figure 6:
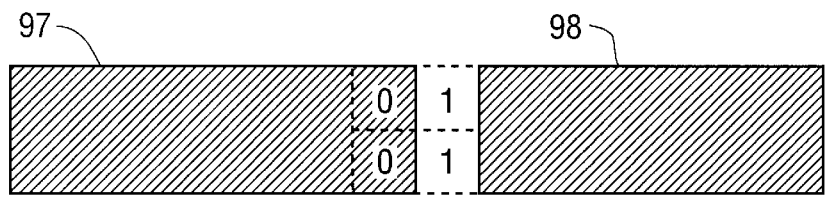
FIG. 6 is a plan view of an opposing pair of leaves configured to apply a dosage specified by the zero degree matrix of FIG. 5.
Figure 7:
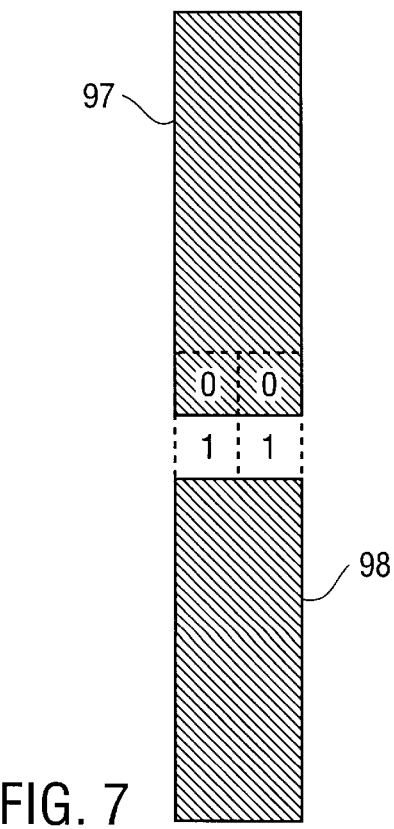
FIG. 7 is a plan view of an opposing pair of leaves configured to apply a dosage specified by the ninety degree matrix of FIG. 5.

FIG. 5 illustrates an example of a matrix, generally indicated at 104 formed from an intensity map composed of four 5 mm×5 mm microcells 106, 108, 110, 112. Each microcell 106, 108, 110, 112 identifies a section in a field to be treated with radiation. The numbers (0, 1, 1, 2) within each microcell 106, 108, 110, 112, respectively, represent the radiation intensity level for locations within the field and are in monitor units (mu) or relative monitor unit intensities (e.g., $1 \times 10^2$ mu). In order to provide 5 mm×5 mm resolution for the intensity map, the matrix 104 is broken down into two orthogonal matrices, 116, 118 having a 1 cm×5 mm resolution and 5 mm×1 cm resolution, respectively. A one centimeter leaf width multi-leaf collimator may then be used to deliver the intensity map with a 5 mm×5 mm resolution. For example, a pair of leaves 97, 98 positioned as shown in FIG. 6 may be used to deliver the map intensity shown in matrix 116 of FIG. 5. A dose of radiation (e.g., 1 mu) is applied to fields corresponding to microcells 108 and 112 of matrix 104. The collimator is then rotated approximately ninety degrees to deliver the map intensity shown in matrix 118 with the leaf position shown in FIG. 7. With the collimator rotated ninety degrees, a dose of radiation (e.g., 1 mu) is applied to the fields corresponding to microcells 110 and 112 of matrix 104. The two radiation applications result in a 2 mu dose to the field corresponding to microcell 112 a 1 mu dose to the fields corresponding to microcells 108 and 110, and no radiation being applied to the field corresponding to microcell 106. The decomposition of the matrix 104 into orthogonal matrices 116 and 118 thus provides for 5 mm×5 mm resolution treatment using collimator leaves having a one centimeter width.

In the following description, the original input intensity map is defined as a macromatrix and the groups of four microcells within the macromatrix are defined as micromatrices (or matrices). In order for the intensity map to be decomposed into orthogonal maps, the vertical gradients of each column of the micromatrix (matrix) 100 must be equal to one another and the horizontal gradients of each row of the micromatrix must also be equal to one another (FIG. 4). This provides a 1 cm×1 cm area under the intersection of one leaf pair for one collimator setting and another leaf pair for the orthogonal collimator setting. For example, if the horizontal gradients are equal for the micromatrix having cells 102 (shown in FIG. 4) the following equation must apply:

$$b-a=d-c;$$

where: a, b, c, d are the intensity values corresponding to locations in the micromatrix 102 of FIG. 4

Similarly, if the vertical gradients are equal the following equation must apply:

$$c-a=d-b.$$

The following describes a method for defining two orthogonal maps, a zero degree map for application with a zero degree offset collimator setting, and a ninety degree map for application with an orthogonal collimator setting. Several decompositions of an intensity map are possible to create the two orthogonal maps. The optimization method described below may be used to find the decompositions which yield the shortest delivery time to minimize overall treatment time and increase the life of the radiation treatment device. Preferably, orthogonal maps having the lowest sum of horizontal gradients (for zero offset maps only) and vertical gradients (for ninety degree offset maps only) are selected through an optimization process to provide matrices resulting in an efficient method of treatment. The following example uses an intensity map represented by a two by four matrix (FIG. 8), however, the intensity map may have a size different than shown herein and may be mapped using various size matrices. Also, the intensity map may be broken down into microcells having a dimension other than 5 mm×5 mm if a different resolution is required. For example, each macrocell may be divided into nine microcells in which case the intensity map may be deliverable as two orthogonal intensity maps having a resolution of 1 cm×⅓ cm and ⅓ cm×1 cm (see, for example, U.S. Pat. application Ser. No. 09/234,364, referenced above). Also, a multi-leaf collimator having leaves with a width other than 1 cm may be used, and the size of the corresponding microcells will be 1/n times the leaf width (where n is a positive integer (e.g., 2 or 3).

FIG. 8 shows a macromatrix V having eight cells, each identified by the row (i) and column (j) that the cell is located in. For example, the upper left hand cell 130 is identified as V1,1 (i=1, j=1) and the lower right hand cell 132 is identified as V2,4 (i=2, j=4). The macromatrix V may be broken down into a uniform matrix U and a microgradient matrix M. The microgradient matrix M is formed by subtracting out from each group of all four cells (micromatrix) the minimum value among them. Thus, the microgradient matrix M will have at least one zero in each group of four cells (micromatrix). The minimum value is then used to create the uniform matrix U, with the following relationship between the original matrix V, uniform matrix U and microgradient matrix M:

$$V=U+M.$$

The macromatrix V is first broken into micromatrices v1,1 and v1,3, each composed of four microcells (FIG. 9). In the following description, the micromatrices v1,1 and v1,3 are identified by the cell located in the upper left hand corner of the macromatrix V (i.e., cells 1,1 and 1,3) and the individual cells within the micromatrices are identified by their original cell location (i,j) in the macromatrix V. The micromatrices v1,1 and v1,3 may then be broken up into uniform matrices u1,1, u1,3 (FIG. 10) and microgradient matrices m1,1, m1,3 (FIG. 11). The uniform matrices are made up of cells having the minimum intensity value of its micromatrix v (i.e., 1 for matrix v1,1 and 3 for matrix v1,3). The uniform matrices u1,1 and u1,3 may therefore, be defined as follows:

$$u1,1=Min(v(2,2), v(2,1), v(1,2), v(1,1)); \text{ and}$$

$$u1,3=Min(v(2,4), v(2,3), v(1,4), v(1,3)).$$

All elements within the uniform matrix ui,j are equal to the minimum value of its micromatrix vi,j:

$$u(2,2)=u(2,1)=u(1,2)=u(1,1); \text{ and}$$

$$u(2,4)=u(2,3)=u(1,4)=u(1,3)$$

The microcells for the microgradient matrix mi,j are calculated as the difference between the respective micromatrix vi,j cells and uniform matrix ui,j cells as follows:

$$m1,1(i,j)=v1,1(i,j)-u1,1(i,j); \text{ and}$$

$$m1,3(i,j)=v1,3(i,j)-u1,3(i,j).$$

The uniform matrices u1,1, u1,3 and microgradient matrices m1,1, m1,3 are each decomposed into two orthogonal subfields, a zero offset field $^0ui,j$, $^0mi,j$ (for application with the same collimator orientation as the original input matrix) and a ninety degree offset field $^{90}ui,j$, $^{90}mi,j$ (for application with the collimator rotated ninety degrees relative to the original input matrix's collimator orientation). The zero offset field and ninety degree offset fields may be defined as follows:

$$mi,j=^0mi,j+^{90}mi,j; \text{ and}$$

$$ui,j=^0ui,j+^{90}ui,j.$$

FIG. 12 shows microgradient matrices for the ninety degree offset field $^{90}m1,1$, $^{90}m1,3$ and the zero degree offset field $^0m1,1$, $^0m1,3$. The ninety degree offset field matrices $^{90}m1,1$, $^{90}m1,3$ each have a resolution of 5 mm×1 cm (i.e., the matrices are configured so that the row elements are equal to one another). The zero degree offset field matrices $^0m1,1$, $^0m1,3$ each have a resolution of 1cm×5 mm (i.e., the matrices are configured so that the column elements are equal to one another). The cell values of the ninety degree offset field matrices $^{90}m1,1$, $^{90}m1,3$ are determined by taking the minimum cell value in each row of the microgradient matrices m1,1 and m1,3, respectively, and setting the other cell in the row equal to the same value. The cell values for the zero degree offset field matrices $^0m1,1$, $^0m1,3$ are determined by finding the smallest value in each column and using the same value for the other cell in the column.

Since the uniform matrices ui,j have gradients equal along both rows and columns, they do not need to be decomposed and can be delivered in combination with the microgradient zero offset field $^0mi,j$. While this is the optimal solution for a single micromatrix v, it is not the most efficient solution when the surrounding micromatrices are taken into account. Thus, it may be more efficient to deliver a portion of the uniform matrix ui,j with the ninety degree offset field $^{90}mi,j$. The amount that is delivered with the zero offset field $^0mi,j$ then becomes a parameter zi,j which is used in an optimization calculation with its values ranging from zero up to the minimum value of the micromatix vi,j (i.e., cell value of ui,j). The parameter zi,j can therefore be defined for each matrix ui,j as follows:

$$^0ui,j(1,1)=^0ui,j(1,2)=^0ui,j(2,1)=^0ui,j(2,2) \text{ zi,j};$$

$$zi,j=0, 1, \ldots, qi,j;$$

where: qi,j=minimum cell value of vi,j.

There are as many parameters in the optimization problem as there are micromatrices. By varying the optimization parameter zi,j many different decompositions may be formed. An example of the possible zero and ninety degree offset uniform matrices $^0u1,1$, $^0u1,3$, $^{90}u1,1$, $^{90}u1,3$ for the macromatrix V of FIG. 8, are shown in FIGS. 13a–13h.

The parameters zi,j may be chosen by using standard optimization algorithms such as simulated annealing, least squares, or downhill simplex method (described in "Numerical Recipes in C" by Vetterling, Press, Flannery, and Teukolsky, 1992, Cambridge University Press). Other optimization methods may also be used. If a starting point is required for the optimization algorithms, zi,j=qi,j/2 may be used.

The optimization involves varying all the zi,j parameters and evaluating the solution in terms of treatment delivery time. Since this is a very involved function that is costly to calculate, a good approximation is to take the maximum sum of the positive gradients along the leaf motion direction for all leaves in both the ninety and zero degree offset fields. For the zero degree offset fields the sum will be taken along the rows of the total zero-offset matrix and for the ninety degree offset fields, the sum will be taken along the columns of the ninety degree offset matrix. Then, the total of the zero degree offset sum and the ninety degree offset sum becomes the function used to choose the best set of parameters. This total sum is preferably minimized.

In order to calculate the positive gradient, a zero is inserted at the beginning of each row and column of the matrix. The gradient is then calculated by adding up positive gradients between adjacent cells. Table 1 shows an example of a positive horizontal gradient calculation for two rows A, B of a matrix. The first row A has a total positive gradient of 2 (0 to 1 for first microcell (+1) and 0 to 1 for third microcell (+1)). Row B has a total positive gradient of 1 (0 to 1 for the first microcell (+1)).

TABLE 1

| A) | 1 | 0 | 1 |
|---|---|---|---|
| B) | 1 | 1 | 1 |

In order to calculate the positive horizontal and vertical gradients for the entire macromatrix V, the respective microgradient matrices $^0m1,1$, $^0m1,3$, $^{90}m1,1$, $^{90}m1,3$ and uniform matrices $^0u1,1$, $^0u1,3$, $^{90}u1,1$, $^{90}u1,3$ are added together to form micromatrices $^0v1,1$, $0v1,3$, $^{90}v1,1$, $^{90}v1,3$. The zero degree offset micromatrices $^0v1,1$, $^0v1,3$ are combined (i.e., placed adjacent one another) to form a total zero degree matrix $^0$T and the ninety degree offset micromatrices $^{90}$v1,1, $^{90}$v1,3 are combined to form the total ninety degree matrix $^{90}$T. The total matrix may be defined as:

$$^0T = {^0U} + {^0M}$$

$$^{90}T\ {^{90}U} + {^{90}M}$$

FIGS. 14a–14h show the total zero and ninety degree offset matrices $^0$T, $^{90}$T corresponding to the different possible uniform matrices shown in FIGS. 13a–13h. The total gradient G is calculated by adding the maximum horizontal gradient across all rows of the total zero degree matrix $^0$T, and the maximum vertical gradient across all columns of the total ninety degree matrix $^{90}$T. The optimum cases are those with the lowest total gradient (i.e., G=6 in FIGS. 14a, 14b, 14f, and 14g). A number of methods may be used to select the final total matrix from the group of total matrices having the lowest total gradient. One method includes using a series of tie breaking functions to select a final intensity map. For example, one tie breaking function that may be used is the total of all gradients in all leaf directions, not just the maximum. Thus, if the function is identified by R, the matrix shown in FIG. 14a has R=12, the matrix of FIG. 14b has R=11, the matrix of FIG. 14f has R=12, and the matrix of FIG. 14g has R=11. Now only the matrices shown in FIGS. 14b and 14g are tied. These matrices may then be put through another function such as the absolute value of the difference between the maximum horizontal gradient and the maximum vertical gradient. With this function defined as D, the matrix of FIG. 14a has D=3−3=0 and the matrix of FIG. 14g has D=4−2=2. Since the matrix of FIG. 14a has a lower function value D, it is selected as the final matrix.

Another tie breaking function that may be used in place of function R for the first pass, is a function X which defines the number of different cell intensity values in each total matrix. For example, the matrix of FIG. 14a includes cell intensity values of 0 and 2 (for $^{90}$T) and 1,2,3, and 4 (for $^0$T), for a function value of X=2+4=6. Similarly, the matrix of FIG. 14b has X=7, the matrix of FIG. 14f has X=6, and the matrix of FIG. 14g has X=7. The matrices of FIGS. 14a and 14f are now tied. The difference function D, described above, may again be used as the second tie breaker. The matrix of FIG. 14a has D=2 and the matrix of FIG. 14f has D=0, thus the final selected intensity map is the matrix of FIG. 14f.

In standard optimization routines, however, only one function is typically used. One way to use the above functions G, R, D, X with a standard optimization routine is to calculate the sum of the functions (e.g., G+R+D or G+X+D). Since each of the functions is to be minimized, the lowest sum will identify the optimum matrix. If there is still a tie at this point, the optimization routine will select one of the matrices depending on its algorithm (e.g., the first lowest one or the last lowest one, depending on the individual algorithm).

Another possible tie breaker method is to use the Bortfield-Boyer segmentation approach to turn the matrices into the set of field shapes required to deliver the intensity map. The set of field shapes yielding the minimum treatment time is then selected as the optimum configuration. If there is a tie, then the set of field shapes with the minimum total beam on time is selected. If there is still a tie, one configuration is arbitrarily selected.

While it is possible to use standard optimization techniques to find the optimum total matrix, an alternative approach is to minimize the gradients along the leaf motion directions in the total matrices $^0$T and $^{90}$T, so that for each iteration of the optimization algorithm, regions of high gradients and the parameter corresponding to that region is changed (i.e., reduced if the region affects a local maximum or increased if the region affects a local minimum).

Although the present invention has been described in accordance with the embodiments shown, one of ordinary skill in the art will readily recognize that there could be variations to the embodiment and these variations would be within the spirit and scope of the present invention. Accordingly, many modifications may be made by one of ordinary skill in the art without departing from the spirit and scope of the appended claims.

What is claimed is:

1. A method for controlling radiation delivery from a radiation source to an object, comprising:

defining a field on the object for radiation delivery, said field including a plurality of cells each having a defined treatment intensity level;

grouping the cells to form a plurality of matrices, each of the matrices having at least one dimension approximately equal to a width of a collimator leaf capable of blocking radiation emitted from the radiation source;

decomposing each of the matrices into orthogonal matrices;

optimizing delivery of the radiation by combining orthogonal matrices from each of the matrices and selecting a combination of orthogonal matrices having minimum vertical and horizontal gradients.

2. The method of claim 1 wherein decomposing the matrix into orthogonal matrices comprises decomposing the matrix into a uniform matrix composed of cells each having an intensity level equal to the minimum cell intensity level of the matrix and a microgradient matrix having cells equal to the intensity level of the cells of the matrix minus the respective cells of the uniform matrix.

3. The method of claim 2 further comprising decomposing the uniform matrix to form a plurality of uniform orthogonal matrices.

4. The method of claim 3 further comprising decomposing the microgradient matrix to form two microgradient orthogonal matrices.

5. The method of claim 4 wherein optimizing delivery of the radiation further comprises adding the uniform and microgradient orthogonal matrices to form said orthogonal matrices and combining said orthogonal matrices of each of the respective matrices to form total orthogonal matrices, the vertical and horizontal gradients being calculated based on the total matrices.

6. The method of claim 1 further comprising defining an opening between the radiation source and said field on the object, said opening being defined by at least two collimator leaves positioned based on the selected orthogonal matrices.

7. The method of claim 6 wherein the cells each have a width and height of approximately one half the width of the collimator leaves.

8. The method of claim 6 wherein each of the collimator leaves has a width of approximately one centimeter.

9. The method of claim 8 wherein the cells each have a width and height of approximately 5 millimeters.

10. The method of claim 6 wherein the opening allows for delivery of said radiation with a resolution of approximately one half the width of the leaves.

11. The method of claim 1 wherein grouping the cells comprises grouping four square cells to form the matrix.

12. The method of claim 1 wherein the orthogonal matrices each have a resolution in a first direction approximately equal to the leaf width and a resolution in a second direction higher than the resolution in said first direction.

13. The method of claim 12 wherein said second direction is generally orthogonal to said first direction.

14. A system for controlling radiation output to an object from a radiation source, said object having a field defined thereon for radiation delivery, said field including a plurality of cells having predefined treatment intensity levels, the system comprising:

a collimator having multiple leaves for blocking radiation from said source and defining an opening between the radiation source and said object; and a processor for receiving the cells, grouping a portion of the cells to form a matrix having at least one dimension approximately equal to a width of one of the collimator leaves, decomposing the matrix into orthogonal matrices, and optimizing delivery of the radiation output by selecting the orthogonal matrices having minimum vertical and horizontal gradients when combined with other orthogonal matrices formed from the remaining cells within the field.

15. The system of claim 14 wherein the leaves of the multi-leaf collimator each have a width of approximately one centimeter.

16. The system of claim 14 wherein the cells have a width and height of approximately one half the width of the collimator leaves.

17. The system of claim 14 wherein the leaves are movable in a first direction generally perpendicular to a delivery direction of the radiation to form said opening between the radiation source and said object, said opening being defined by at least two of the collimator leaves positioned based on the selected orthogonal matrices.

18. The system of claim 17 wherein the leaves are movable in a second direction generally perpendicular to said delivery direction and said first direction.

19. The system of claim 17 wherein the multi-leaf collimator is operable to provide radiation treatment with a resolution approximately one half of the width of the leaves.

20. The system of claim 14 wherein vertical gradients of the matrix are equal to one another and horizontal gradients of the matrix are equal to one another.

* * * * *